United States Patent [19]

Wonder

[11] 4,311,146

[45] Jan. 19, 1982

[54] DETACHABLE BALLOON CATHETER APPARATUS AND METHOD

[75] Inventor: Terry M. Wonder, Salt Lake City, Utah

[73] Assignee: Sorenson Research Co., Inc., Salt Lake City, Utah

[21] Appl. No.: 147,814

[22] Filed: May 8, 1980

[51] Int. Cl.³ .............................................. A61M 25/00
[52] U.S. Cl. ...................................... 128/325; 29/454; 29/460; 264/264; 128/344; 427/2; 427/282
[58] Field of Search .................... 128/325, 344, 349 B, 128/349 BV; 251/61.1; 138/93; 128/DIG. 16

[56] References Cited

U.S. PATENT DOCUMENTS

| | | |
|---|---|---|
| 600,967 | 3/1898 | Mead . |
| 2,043,630 | 6/1936 | Raiche .................................. 264/264 |
| 2,493,326 | 1/1950 | Trinder . |
| 2,930,377 | 3/1960 | Cowley . |
| 3,030,953 | 3/1962 | Koehn . |
| 3,039,468 | 6/1962 | Price . |
| 3,108,593 | 10/1963 | Glassman . |
| 3,334,629 | 8/1967 | Cohn . |
| 3,435,826 | 4/1969 | Fogarty . |
| 3,448,739 | 6/1969 | Stark et al. . |
| 3,452,756 | 7/1969 | Harautuneian .................. 264/264 X |
| 3,467,101 | 9/1969 | Fogarty et al. . |
| 3,512,528 | 5/1970 | Whitehead et al. . |
| 3,539,674 | 11/1970 | Dereniuk et al. ................ 264/264 X |
| 3,540,431 | 11/1970 | Uddin . |
| 3,544,668 | 12/1970 | Dereniuk ........................ 264/264 X |
| 3,625,793 | 12/1971 | Sheridan et al. ................ 156/294 X |
| 3,642,004 | 2/1972 | Ostahgen et al. . |
| 3,795,240 | 3/1974 | Sturgeon . |
| 3,833,003 | 9/1974 | Taricco . |
| 3,834,394 | 9/1974 | Hunter et al. ....................... 128/325 |
| 3,850,176 | 11/1974 | Gottschalk ........................ 128/325 |
| 3,850,720 | 11/1974 | Collins ............................ 156/294 X |
| 4,029,104 | 6/1977 | Kerber . |
| 4,085,757 | 4/1978 | Pevsner ............................. 128/325 |
| 4,122,869 | 10/1978 | Roberson ............................. 138/93 |
| 4,137,906 | 2/1979 | Akiyama et al. ................... 128/325 |
| 4,160,448 | 7/1979 | Jackson . |
| 4,265,848 | 5/1981 | Rüsch ............................ 264/264 X |

FOREIGN PATENT DOCUMENTS

| | | |
|---|---|---|
| 581453 | 8/1958 | Italy . |
| 782496 | 9/1957 | United Kingdom . |
| 542523 | 2/1977 | U.S.S.R. ..................... 128/DIG. 16 |

OTHER PUBLICATIONS

Kerber et al., "Calibrated Leak Balloon Microcatheter, etc." *Amer. Journal of Radiology,* pp. 207–212; Feb., 1979.

White et al., "Therapeutic Embolization with Detachable Silicone Balloons", 241 *JAMA* 1257–1260; Mar. 23, 1979.

White et al., "Therapeutic Embolization with Detachable Balloons", *Work in Progress,* pp. 521–523; Feb. 1978.

Kaufman et al., "Therapeutic Embolization with Detachable Silicone Balloons, etc.", *Investigative Radiology,* 156–161.

Serbinenko, "Balloon Catheterization, etc.", *Journal of Neurosurgery,* vol. 41, pp. 125–145; Aug., 1974.

Leussenhop–Intra-Arterial Instrumentation, etc.", "*Bulletin of the Dow-Corning Ctr. for Med. Research;* Jul. 1, 1960.

J. Guillaume et al., "Experimental Embolization, etc." *Neuroradiology, 14; 85–88; 1977.*

M. H. Wholey, "The Technology of Balloon Catheters, etc.", *Diagnostic Radiology,* pp. 671–676; Dec. 1977.

DiTullio, M. V., et al., "Detachable Balloon Catheter", 48 *Journal of Neurosurgery,* pp. 717–723 (1978).

DiTullio et al., "Development of a Detachable Vasuclar Balloon Catheter, 41 *Bull. of the Los Angeles Neurological Soc.,* pp. 2–5; 1976.

*Medical Product Salesman*–(News Item) "Catheter Assists in New Surgical Technique"; Nov. 1978.

Debrun et al., "Experimental Approach, etc." 9 *Neuroradiology,* pp. 9–12; (1975).

Berenstein et al., "Catheter and Material Selection, etc.", 132 Neuroradiology, 619–639; September 1979.

*Primary Examiner*—F. Barry Shay
*Attorney, Agent, or Firm*—H. Ross Workman; Rick D. Nydegger

[57] ABSTRACT

A detachable balloon catheter apparatus and method.

The apparatus includes an introducer catheter which is attached at its trailing end to a source of pressurized fluid. The leading end of the catheter is attached to an inflatable balloon which may be inflated as the pressurized fluid is injected through the introducer catheter. A valve mechanism is positioned inside the assembled introducer catheter and balloon and the leading end of the valve mechanism is bonded to the interior of the balloon. As the balloon is inflated by the pressurized fluid, a forwardly directed lateral force is exerted on the valve mechanism so that it is pulled forward into fluid-tight engagement with the valve seat placed at the opening of the balloon. Once the valve mechanism is pulled into fluid-tight engagement so as to close off the opening of the balloon, further injection of the pressurized fluid serves to detach the inflated balloon from the introducer catheter.

22 Claims, 9 Drawing Figures

Fig. 1
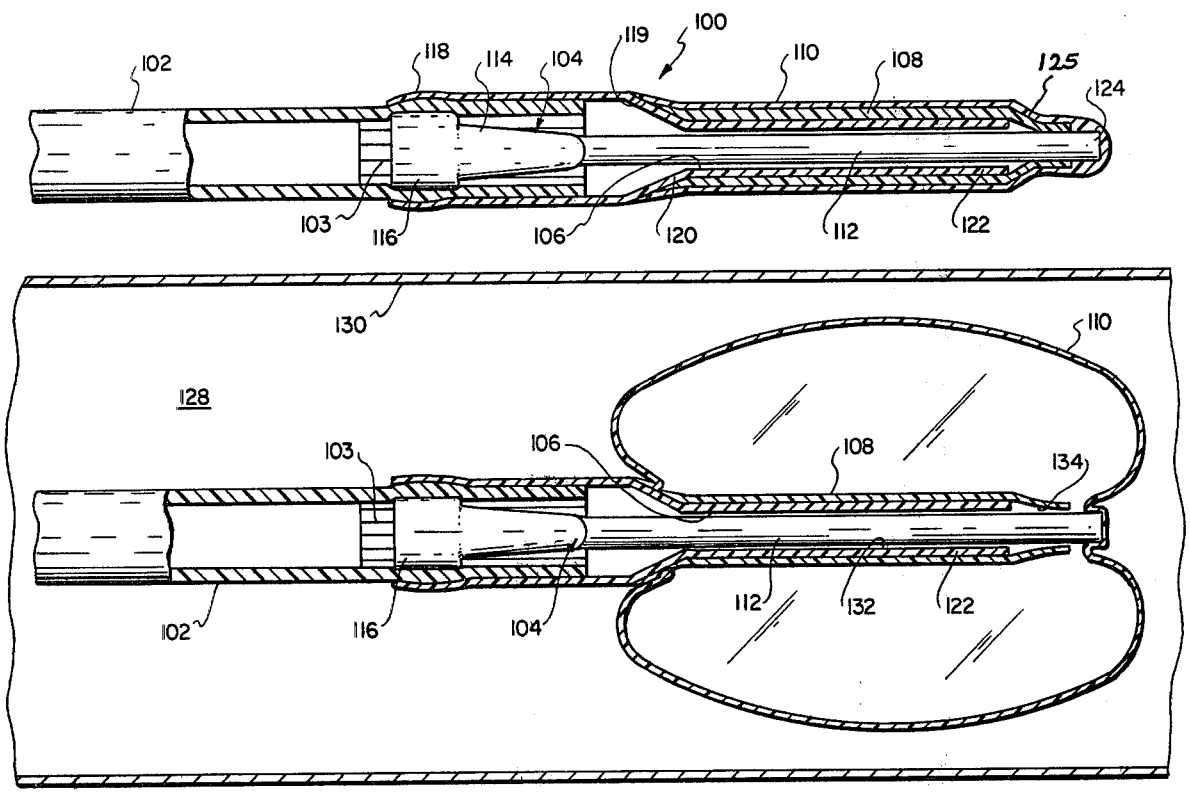
Fig. 2
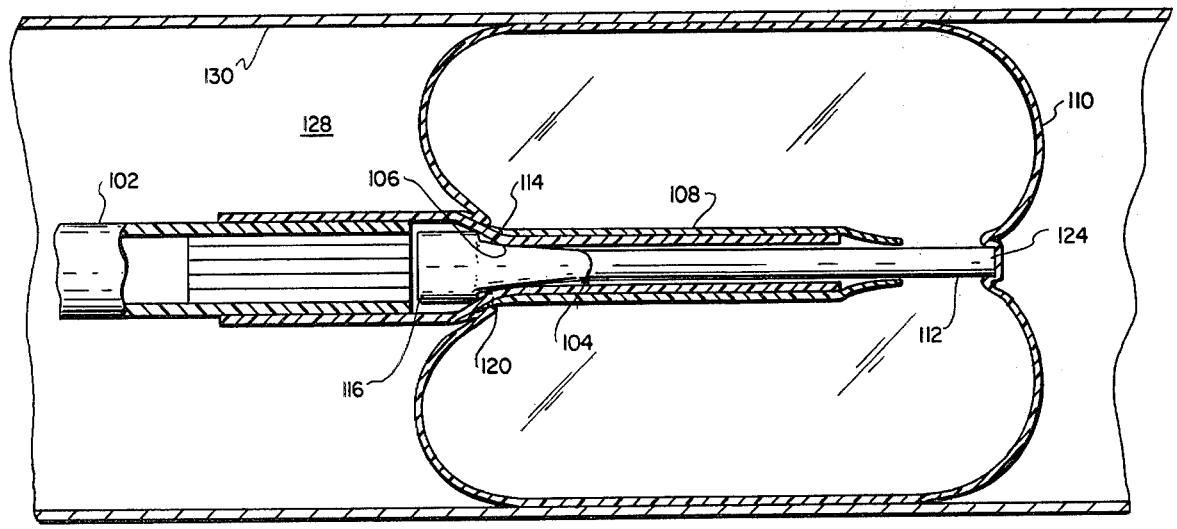
Fig. 3

DETACHABLE BALLOON CATHETER APPARATUS AND METHOD

BACKGROUND

1. The Field of the Invention

The invention relates to balloon catheters, and more particularly to a balloon catheter wherein the balloon, after inflation, can be automatically sealed and detached from the catheter.

2. The Prior Art

Balloon catheters have been available since about 1950 and have been used in such diverse medical techniques as arterial emboli extraction, venous thrombectomy, and removal of biliary calculi. Furthermore, percutaneous balloon catheters have been developed for interventional angiography and have been utilized to control hemorrhage, operative angiography, conventional embolectomy, vena cava occlusion, and intentional vascular thrombosis or dearterialization.

In recent years, there has been considerable interest in developing detachable balloon catheters for use in surgical procedures that involve vascular occlusion, e.g., occlusion of carotid-cavernous sinus fistulas and other arterio-venous malformations, particularly those involving intracranial circulation. Heretofore, repair of cerebral aneurysms and arteriovenous fistulas has required radical brain surgery, despite the fact that such surgery is necessarily dangerous and complicated. For example, it is not uncommon for such surgery to result in the destruction of valuable portions of the brain in order to get to the aneurysm, often resulting in partial paralysis or loss of some vital autonomic function. Hence, heretofore a patient afflicted with a cerebral aneurysm or fistula was often required to choose between the risk of loss of his life if he elected not to undergo surgery, or the risk of a future of less than full use of his faculties in the event that he elected surgical correction of the problem.

Recently it has been found that radical surgery can be eliminated and inoperable aneurysms can be corrected through a safe and efficient technique involving a detachable balloon catheter. The catheter is "snaked" through the artery to the point of the aneurysm, the balloon is inflated until it occludes the vascular lumen, and the balloon is detached so that the catheter can be removed. The detached balloon is employed to obstruct the venous outflow tract and to artificially reconstitute the damaged wall of the cavernous segment of the involved carotid artery. Unfortunately, routine utilization of this valuable technique has been thwarted by the lack of a reliable apparatus.

The problem which has faced those skilled in the art is how to inflate the balloon after it is in position and then reliably seal the balloon and detach it from the catheter while it remains in position without damaging the balloon or the surrounding tissue. Although various attempts to solve this problem have been made by those skilled in the art, to data there has not been devised an apparatus and method that have fully succeeded in achieving a solution to this problem.

For example, one prior art approach to the problem has been to inflate the balloon, leave the catheter attached to the balloon extending through the artery, seal the catheter, and tie the catheter off at a place remote from the aneurysm, such as the point of entry into the artery. See, e.g., Prolo et al., "Balloon Occlusion of Carotid-Cavernous Fistula: Introduction of a New Catheter," 7 *Surgical Neurology* 209-13 (April 1977).

The technique has several significant drawbacks. Chief among them is that the catheter must remain in the artery as long as the balloon is to remain in position, thereby obstructing the flow of blood in the artery. This may be particularly disadvantageous since the artery involved is often the carotid artery—the source of blood flow to the brain. Leaving the catheter in the artery also opens up the possibility of several other medical problems caused by a foreign object in the delicate portions of the brain. Also, researchers have had trouble in keeping such a balloon inflated over a long period of time.

Another prior art approach to the problem has been to use a double lumen catheter design in order to detach the balloon from the catheter. In this approach a small latex balloon is tied to the end of a catheter by thin latex threads under tension and a second catheter is provided surrounding the first inner catheter. The inner catheter is manipulated into position and the balloon is inflated. The outer catheter is then positioned snugly against the base of the balloon and the inner catheter is pulled backwards, separating the balloon from the inner catheter while the tightly wound latex threads at the base of the balloon keep it inflated. See generally, Fierstien et al., "Complete Obliteration of a Carotid Cavernous Fistula With Sparing of the Carotid Blood Flow Using a Detachable Balloon Catheter," 9 *Surgical Neurology* 277-80 (May 1978); Debrun et al., "Endovascular Occlusion of Vertebral Fistulae by Detachable Balloons With Conservation of the Vertebral Blood Flow," 130 *Radiology* 141-47 (January 1979).

Although this technique has advantages as compared to leaving the catheter attached to the inflated balloon, several disadvantages have been observed. Unless a solidified filler, such as silicone, is used to inflate the balloon, it has been found that the fluid will gradually diffuse out of the balloon, collapsing it within two or three weeks after implantation. However, solidified filler is difficult and awkward to work with and results in a permanently hardened balloon. Since the catheter is initially inserted into the balloon during inflation, when the catheter is removed the volume of the balloon decreases by a volume representing the dead space of the catheter. Other problems have been observed, including premature separation of the balloon from the catheter, migration or other unwanted effects secondary to the permanent implantation of the balloon, and the risk of bursting of the balloon during the inflation step.

Another approach that has been tried is the use of a balloon that is attached to the tip of a double lumen catheter by means of a metal tube. The distal half of the metal tube is tapered so that it can penetrate into an elongated, solid neck portion on the balloon. After the balloon is inflated, the metal tube can be withdrawn by using the outer catheter and the thickened rubber portion of the balloon will self-seal. See Liliequist et al., "Occlusion of the Carotid Artery Using Catheter With Detachable Balloon In Pigs," 20 *Acta Radiologica Diagnosis* 100-04 (January 1979); Laitinen et al., "Embolization of Cerebral Vessels With Inflatable and Detachable Balloons," 48 *J. Neurosurgery* 307-08 (February 1978).

The problems encountered with this design are similar to those discussed above. The main problem has been leakage of the balloon, which may not be apparent until as long as one or two weeks after implantation. Furthermore, there have been cases of balloon damage during passage through the outer guiding catheter, and there have been instances of rupture of the balloon after the catheter had been withdrawn.

Yet another approach to the problem has been to use a balloon that is attached to the catheter by a C-shaped spring clamp. See, e.g., U.S. Pat. No. 4,085,757. After the balloon has been inflated to seal the vascular lumen, additional fluid is injected into the balloon increasing the pressure until the balloon squirts off of the end of the catheter. The C-spring clamp then closes off the opening in the balloon left by the retracted catheter.

Again, this approach has resulted in certain drawbacks. In particular this design results in an excessive pressure exerted on the walls of the vessel at a point near the aneurysm or fistula in order to detach the balloon. Furthermore, an accurate determination of the ultimate size of the balloon is difficult and movement of the balloon during the detachment step is possible (as well as injury to the vessel during such movement).

In summary, the problems discussed above have posed significant obstacles to the development of a detachable balloon catheter that is safe, simple, and effective in its operation, thus preventing routine diagnostic and/or therapeutic use of the balloon catheter despite the otherwise significant advantages that may be obtained through such use.

BRIEF SUMMARY AND OBJECTS OF THE INVENTION

The present invention is directed to a detachable balloon catheter apparatus and method for use in a vascular membrane, such as a human blood vessel. The balloon catheter includes a novel valve assembly within and/or attached to the distal end of the introducer catheter, and an inflatable balloon which is securely affixed to a portion of the valve assembly. The balloon assembly is introduced into the vessel by a single lumen catheter until it is properly positioned. Fluid injected through the introducer catheter operates to inflate the balloon until it is securely positioned in the vessel. The valve assembly is responsive to the fluid pressure in the inflatable balloon so that when the pressure within the balloon reaches a predetermined amount, the valve assembly actuates to automatically seal the balloon. A further increase in the fluid pressure within the introducer catheter then serves only to separate the balloon and the valve assembly from the introducer catheter, which can then be withdrawn.

It is, therefore, an object of the present invention to provide a detachable balloon catheter apparatus and method which can be safely used for permanent and precise occlusion of a vascular membrane, such as a human blood vessel.

Another important object of the present invention is to provide a detachable balloon catheter apparatus and method which uses a single lumen introducer catheter in an operative technique that is fast, simple, minimizes the risk of rupture and/or migration of the detached balloon assembly, and precludes excessive pressure from being exerted on the walls of the vascular membrane.

These and other objects and features of the present invention will become more fully apparent from the following description and appended claims taken in conjunction with the accompanying drawings.

BRIEF DESCRIPTION OF THE DRAWINGS

FIG. 1 is a longitudinal cross-sectional view of a presently preferred embodiment of the detachable balloon catheter assembly of the present invention showing the assembly prior to inflation of the balloon.

FIG. 2 is a longitudinal cross-sectional view of the embodiment of FIG. 1 illustrating the detachable balloon catheter assembly positioned within the lumen of a blood vessel and showing the balloon in a state of partial inflation before the valve mechanism is actuated to seal the balloon.

FIG. 3 is a longitudinal cross-sectional view of the embodiment of FIG. 1 illustrating the detachable balloon catheter assembly within the lumen of a blood vessel and showing the balloon in a state of full inflation after it has been sealed by the valve mechanism.

DETAILED DESCRIPTION OF THE PREFERRED EMBODIMENTS

Figure 4:
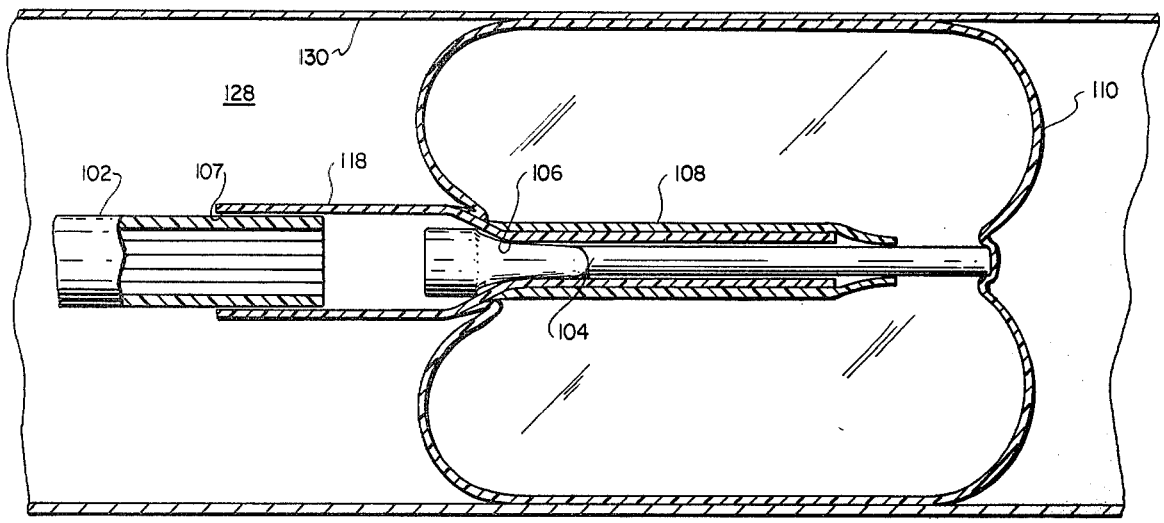
FIG. 4 is a longitudinal cross-sectional view of the embodiment of FIG. 1 illustrating the detachable balloon catheter assembly within the lumen of a blood vessel and showing the beginning of the separation of the introducer catheter from the fully inflated balloon.

Reference is now made to the drawings wherein like parts are designated with like numerals throughout. Referring more particularly to FIG. 1, the detachable balloon catheter apparatus of the present invention, generally designated 100, consists of a single lumen introducer catheter 102, a valve mechanism generally designated 104, a valve seat 106, a masking sleeve 108 and an inflatable balloon 110.

Introducer catheter 102 is elongated, has a small diameter and is made of a moderately flexible material, such as silastic or polyurethane. The flexibility of the material is chosen so that the catheter can be digitally maneuvered or "snaked" through the human blood vessels, particularly the intracranial arteries. The introducer catheter is open at both ends with the trailing end having a fitting (not shown) for connection to a conventional source of pressurized fluid, such as a syringe (not shown) containing a saline or radiopaque solution.

At its leading end the interior of the introducer catheter 102 is provided with a plurality of fluid channels that are formed by longitudinal ribs 103. The fluid channels formed by ribs 103 provide fluid passageways around an enlarged valve head 116 positioned inside the leading end of introducer catheter 102, so that fluid may be injected into the balloon 110 to inflate it, as described in greater detail below. The longitudinal ribs 103 may be straight or slightly arcuate. Alternatively, the leading end of catheter 102 may have a smooth interior lumen and the enlarged valve head 116 may be provided with grooves or ribs to form the desired fluid channels.

The dimensions of the introducer catheter 102 and the detachable balloon assembly are a matter of design choice depending upon the size of the particular blood vessel or cavity in which it is to be used. For example, the apparatus 100 may be used to occlude very small blood vessels, as in the brain, where the largest diameter of the apparatus prior to inflation may be approximately 0.025 inch (0.64 mm). Or, the apparatus 100 may be used to occlude larger blood vessels or even cavities, such as found in a kidney, an intestinal tract or the fallopian tubes.

The valve mechanism 103 includes an elongated stem portion 112 at its leading end. The trailing end of the valve mechanism 104 is flared as at 114 and is joined to an enlarged head portion 116. Enlarged valve head 116 preferably fits snugly within the leading end of the introducer catheter 102 and may cause a portion of the introducer catheter 102 to be slightly stretched.

The valve seat 106 has a trailing end that is enlarged and expanded to form a collar 118 which frictionally fits over the leading end of the introducer catheter 102 and valve head 116. Because of the interferring fit between enlarged valve head 116, introducer catheter 102, and collar 118, the valve mechanism 104, valve seat 106 and balloon 110 remain attached to the introducer catheter 102 during insertion into a blood vessel until detachment of the balloon is desired, as described in more detail below.

Collar 118 tapers at 120 and terminates in a tubular, elongated leading end 122 that fits telescopically over the stem 112 of valve mechanism 104. As more fully described below, the elongated, tubular end 122 is somewhat shorter in length than the valve mechanism 104 so that the forward tip 124 of the stem 112 will extend beyond the leading end 122 of valve seat 106, permitting the forward tip 124 of valve mechanism 104 to be bonded to the interior surface of the balloon 110. Also, the diameter of the stem 112 is slightly less than the inside diameter of the elongated leading end 122 of valve seat 106 so that the pressurized fluid injected into the balloon 110 may easily pass therethrough.

Valve seat 106 is preferably made of a flexible polyurethane material, but may also be made of polyvinyl chloride or other suitable material. Valve mechanism 104 is preferably made of a material harder than the valve seat 106, such as a hard urethane or polyvinyl chloride material so that a fluid-tight seal can be formed between the valve mechanism 104 and the valve seat 106.

The inflatable balloon 110 encloses the stem 112 of valve mechanism 104 and the elongated leading end 122 of valve seat 106. The balloon 110 is bonded at its opening 119 to the tapered portion 120 of collar 118. The interior surface of balloon 110 is bonded to the forward tip 124 of valve stem 112, for purposes of actuating the valve mechanism 104, as will be hereinafter described in more detail.

Inflatable balloon 110 is made of a suitable elastomeric material, such as polyurethane, latex rubber, or silicone. Polyurethane is presently preferred because of its high strength, resistance to chemical and biological degradation, low membrane porosity, and its high degree of compatability with a variety of different fluids that may be used to inflate the balloon.

Although the balloon 110 could be performed and then attached to the valve seat 106 by an adhesive, the balloon 110 is preferably formed by placing a thin (typically 0.001 inch (0.025 mm) thick) masking sleeve 108 snugly over the leading end 122 of valve seat 106. The masking sleeve 108 preferably is stretched so that its forward end 125 will taper, thus completely enclosing the leading end 122 of the valve seat 106 while still leaving the forward tip 124 of valve stem 112 exposed.

When the valve mechanism 104, collar 118 of valve seat 106 and masking sleeve 108 have been assembled and attached to the leading end of catheter 102, the assembly is then dipped into a solution of polyurethane or other suitable elastomeric material. The assembly is dipped into the solution up to the tapered portion 120 of valve seat 106, slightly beyond termination of the trailing end of masking sleeve 108. Since the masking sleeve 108 is made from tetrafluorethylene-hexafluoropropylene copolymer (teflon) or other material which will not bond to the elastomeric dipping solution, the balloon 110 will only be bonded to the assembly at the forward tip 124 of the valve stem 112 and at the tapered portion 120 of valve seat 106 which are not covered by the masking sleeve 108.

It may be necessary to repeat the dipping operation once or twice to form a membrane thick enough to withstand a particular inflation pressure. Moreover, it will be appreciated that by varying the composition and concentration of the elastomeric balloon-forming solution and the length of the masking sleeve 108, it is possible to vary the thickness and the ultimate size of the inflated balloon. Hence, the device of the present invention may be designed so that the size and shape of the resulting balloon can be predetermined and the medical surgeon can choose a balloon which will be properly sized and shaped for the particular vessel or cavity in which it will be used.

The method of detachment of the balloon assembly from the introducer catheter can be best understood with reference to FIGS. 2-5.

Typically the apparatus 100 of the present invention is introduced into the lumen 128 of a blood vessel 130 by first passing a catheter (not shown) of larger diameter into the vessel 130 at the point of entry (not shown). Introducer catheter 102 is then passed through the larger catheter (not shown) and is "snaked" through the vessel 130 to the point where it is desired to occlude the vessel 130. The larger catheter (not shown) can be removed or retained in position during this procedure.

It may be desirable to partially inflate the balloon 110 with a small amount of radiopaque fluid in order to permit fluoroscopic visualization of the balloon as it is maneuvered into place. Alternatively, a portion of the device, such as the valve mechanism 104, could be made of a radiopaque material or a silver particle may be embedded in the valve mechanism 104 to allow for fluoroscopic visualization.

As shown in FIG. 2, once the detachable balloon assembly has been positioned at the point where occlusion of the vessel 130 is desired, pressurized fluid is injected through the introducer catheter 102 and into the balloon 110 so that it will begin to inflate.

It will be appreciated that there are a number of different types of perfusate fluids that may be used. For example, radiopaque compounds may be preferred to enable visualization during insertion and placement of the balloon. Also, isotonic solutions may be preferred so as to minimize tendencies toward osmotic diffusion across the balloon membrane. It is also within the scope of the present invention to use a solidified filler material, such as silicone, which can be made to solidify after the balloon 110 is in position.

The pressurized fluid will flow through the fluid channels formed by ribs 103 around the enlarged valve head 116. The fluid will then flow to the interior of the balloon 110 through a passageway 132 formed in the clearance area between valve stem 112 and the surrounding leading end 122 of valve seat 106, and through a slight clearance space 134 between sleeve 108 and valve stem 112 caused by the fluid pressure.

With further reference to FIG. 2, as the balloon 110 starts to inflate, it will expand longitudinally, as well as radially outward from the valve stem 112. As shown in FIG. 3, the radial expansion is limited by the internal diameter of the blood vessel 130 thereby causing the principal mode of expansion to be longitudinal. Since the forward tip 124 of valve stem 112 is bonded to the interior of the balloon 110, longitudinal expansion of the balloon 110 will exert a force on the valve stem 112 (and accordingly, on the entire valve mechanism 104) which will cause the valve mechanism 104 to move laterally forward.

When the lateral force exerted on the valve mechanism 104 becomes greater than the coefficient of static friction holding enlarged valve head 116 within the leading end of introducer catheter 102, the valve mechanism 104 wll be withdrawn from the introducer catheter 102 into frictional engagement with the tapered portion 120 of valve seat 106. It has been found that when the balloon 110 is inflated to its optimum size, the valve mechanism 104 actually "snaps" into the valve seat 106 as though it were spring-loaded, thereby jamming the tapered portion 114 of the valve mechanism 104 into the tapered portion 120 of valve seat 106, forming a fluid-tight seal.

Figure 5:
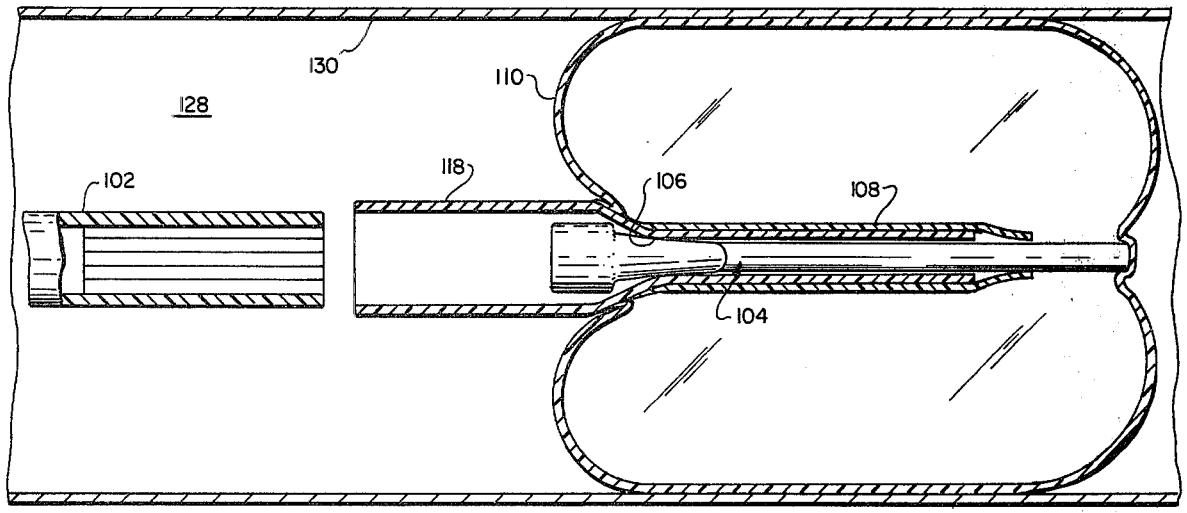
FIG. 5 is a longitudinal cross-sectional view of the embodiment of FIG. 1 illustrating the detachable balloon catheter assembly within the lumen of a blood vessel and showing complete detachment of the inflated balloon and valve assembly from the introducer catheter.

As shown in FIG. 4, once the valve mechanism 104 has engaged the valve seat 106 in a fluid-tight seal, any additional injection of fluid into the introducer catheter 102 will force th collar 118 of valve seat 106 to expand, creating a small passageway 107 between the introducer catheter 102 and collar 118. It should be observed that the walls of valve seat 106 are specifically constructed so that they will be thinner or made of softer, more compliant material so that they will be more apt to expand than the walls of introducer catheter 102. Thus, the remaining frictional attachment between the introducer catheter 102 and the collar 118 is reduced once the enlarged head portion 116 of valve mechanism 104 is separated from the introducer catheter 102. Hence, as shown in FIG. 5 the fluid pressure acts to separate the collar 118 from the introducer catheter 102 by means of the reduced frictional attachment and by means of the lubricity of the fluid flowing through passageway 107 thus detaching the balloon 110 from the introducer catheter 102 which can then be withdrawn from the vessel 130.

Also, it will be recognized that the more compliant balloon material will expand at a lesser pressure than is required to expand the collar 118 of valve seat 106, thus insuring that the balloon assembly remains attached to the introducer catheter until fully inflated.

It will be appreciated that no additional pressure is exerted by the inflated balloon 110 against the walls of the blood vessel 130 during the detachment procedure. Thus, the apparatus and method of the present invention eliminate the risk of bursting the balloon due to over inflation when attempting to detach the balloon from the introducer catheter. In other words, the balloon is automatically sealed when it reaches the predetermined amount of inflation necessary to occlude the blood vessel, so that further injection of fluid serves only to detach the balloon rather than further inflating it, as in the prior art type devices.

It will be further appreciated that the apparatus and method of the present invention alleviates many of the other problems encountered with prior art devices. Unlike most prior art devices, the present invention is not subject to slow leaking of the fluid from the valve assembly causing it to collapse within a few weeks after implantation. There are essentially two reasons for this improvement over the prior art: (1) the mating of the valve mechanism 104 in the valve seat 106 provides a greater surface area of contact than in prior art devices, and (2) the longitudinal expansion forces exerted by the balloon 110 on the valve mechanism 104 tend to continuously urge the valve mechanism 104 into a closed, fluid-tight position in the valve seat 106. Accordingly, the greater the forces placed upon the balloon 110 by the blood vessel 130, the stronger the sealing effect of the valve mechanism 104.

Also, due to the improved method of attachment of the balloon from the introducer catheter there is little likelihood of premature separation of the balloon 110 from the introducer catheter 102. There is also little likelihood of migration of the balloon during the detachment operation since the balloon has already been inflated tightly against the vessel walls and sealed before the introducer catheter is separated. Further, there are no tugging forces applied to the balloon while effecting detachment, which would increase the risk of bursting or dislodging the balloon.

It will be appreciated that another major advantage of the present invention is that only a single lumen introducer catheter is necessary, which is both smaller in diameter and more flexible than a double lumen catheter, thus permitting its use in smaller diameter blood vessels.

Moreover, in a single procedure, that is, by injecting increasing amounts of fluid through the introducer catheter, the surgeon may inflate, seal and detach the balloon from the catheter. This operative procedure is thus fast, simple, and safe.

Figure 6:
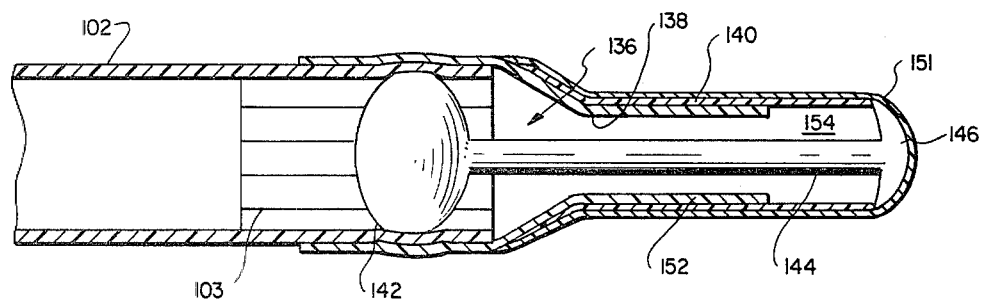
FIGS. 6-9 are longitudinal cross-sectional views of alternative embodiments of the detachable balloon catheter apparatus of the present invention.
Figure 7:
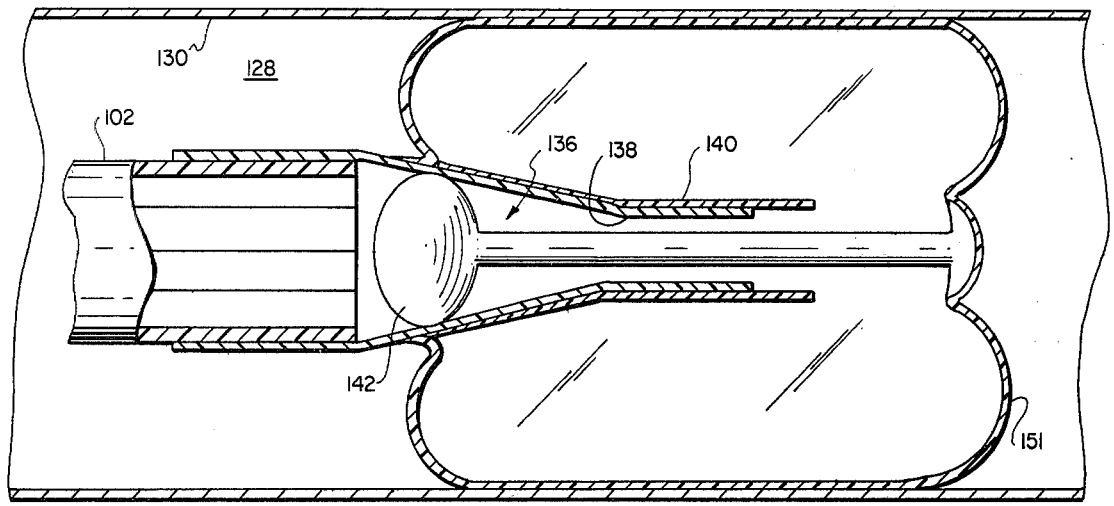

Another embodiment of the apparatus and method of the present invention is illustrated in FIGS. 6 and 7. The detachable balloon catheter apparatus illustrated in those figures differs from the apparatus previously described primarily in the configuration of the valve mechanism. As shown in FIG. 6 the valve mechanism generally designated 136 consists of an enlarged head portion 142 and an elongated stem portion 144. The forward tip of the valve stem 144 terminates in a button 146. The button 146 may be formed by heating the end of valve stem 144 and then compressing it while it is still heated.

With further reference to FIG. 6, it will also be seen that the valve seat 138 is diametrally enlarged in relation to the valve stem 144. The diametrally enlarged valve seat 138 permits the size and shape of the balloon to be varied, as hereinafter described in more detail.

The masking sleeve 140 is snugly fit over the leading end 152 of the valve seat 138 and extends out to the flat button 146 formed at the forward tip of the valve stem 144. Further, it will be noted that the diameter of the flat button 146 corresponds to the diameter of the masking sleeve 140 so as to prevent the dipping solution for the balloon from entering into the space 154 formed between the masking sleeve 140 and valve stem 144. Thus, when the valve mechanism 136, valve seat 138 and masking sleeve 140 are assembled and attached to the leading end of catheter 102, the assembled components are then dipped into a urethane solution so as to form the membrane for the balloon 151. As with the prior embodiment, the balloon 151 will adhere only to the surface of the flat button 146 provided at the forward tip of the valve stem 144 and the portion of the valve seat 138 that are not covered by the masking sleeve 140.

Operation of the embodiment of the detachable balloon catheter apparatus illustrated in FIG. 6 is best understood with reference to FIG. 7. As shown in FIG. 7 injection of the pressurized fluid causes the balloon 151 to inflate. As the balloon 151 radially expands it eventually engages the walls 130 of the blood vessel which then causes the balloon 151 to expand longitudinally. As the balloon 151 expands longitudinally a forwardly directed longitudinal force is increasingly exerted at the flat button 146 attached to the valve stem 144. When the coefficient of static friction between the enlarged valve head 142 and the leading end of introducer catheter 102 is exceeded by this forwardly directed longitudinal force, the valve mechanism 136 is forcefully driven into fluid-tight engagement with the valve seat 138 in the same manner as previously described.

Figure 8:
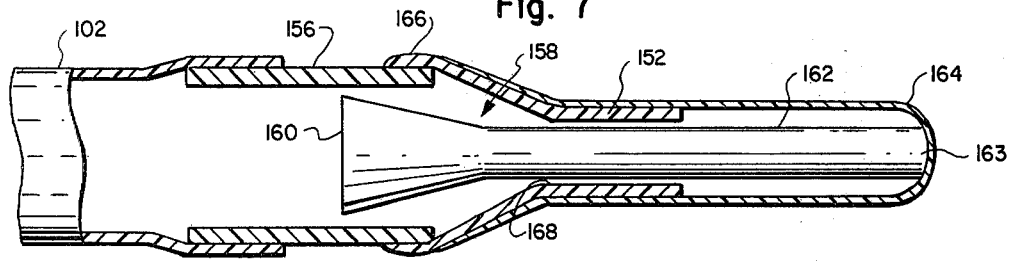
Figure 9:
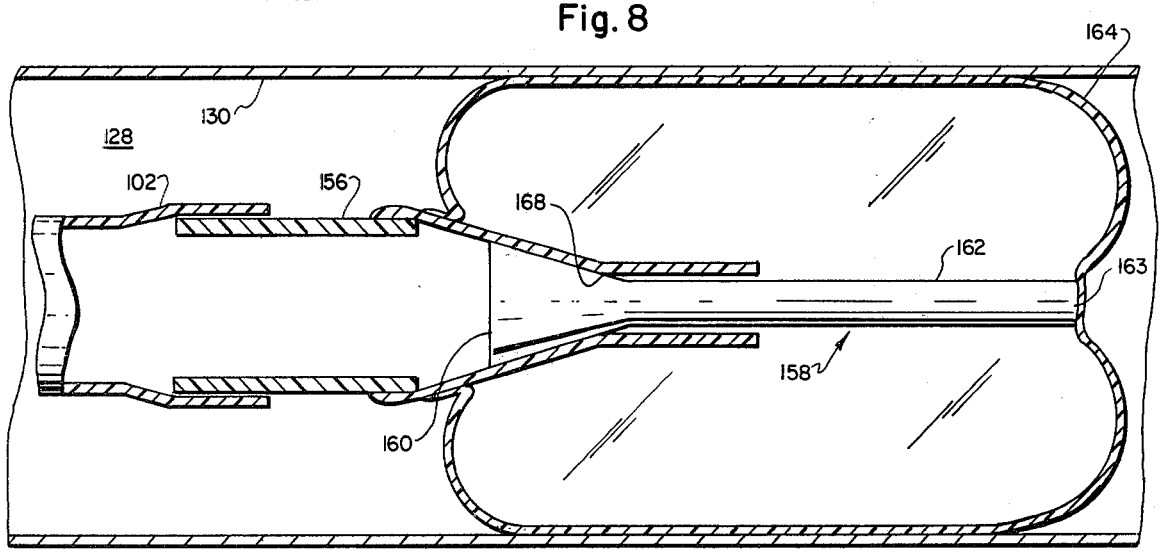

Another embodiment of the detachable balloon catheter apparatus of the present invention is illustrated in FIGS. 8 and 9. As shown in FIG. 8 the valve mechanism generally designated 158 has an elongated stem 162 that is bonded at its forward tip 163 to the interior of the balloon 164. The trailing end of valve mechanism 158 terminates in an enlarged head portion 160 that is tapered and joined to the valve stem 162. The enlarged head portion 160 is diametrially reduced in relation to the inside diameter of connecting tube 156. Connecting tube 156 is constructed of a semi-rigid plastic material which is somewhat less elastic than the introducer catheter 102. Introducer catheter 102 is stretched at its leading end so as to frictionally fit over the trailing end of the connecting tube 156. The leading end of connecting tube 156 is permanently bonded to the collar portion 166 of valve seat 168. In the embodiment illustrated in FIG. 8, the balloon 164 is pre-formed and is bonded to the valve seat 168 along the tapered portion thereof and at the forward tip 163 of valve stem 162, as previously indicated.

Fluid injected through the introducer catheter 102 will flow around the enlarged head portion 160 since it is diametrially reduced in relation to the inside diameter of connecting tube 156. The fluid will then flow through the elongated leading end 152 of valve seat 168 into the interior of the balloon 164, thus inflating the balloon 164. As shown best in FIG. 9, when the balloon 164 becomes fully inflated radial expansion will be limited by the walls 130 of the blood vessel causing the expension to be longitudinal, as with the previously described embodiments. The longitudinal expansion will exert a force on the valve stem 162 which is attached at its forward tip 163 to the interior of the balloon 164, pulling the valve mechanism 158 forward until the enlarged head portion 160 is tightly seated in fluid-tight engagement with the tapered portion of the valve seat 168. Once the valve mechanism 158 is seated in fluid-tight engagement with the valve seat 168 further injection of fluid will cause the leading end of introducer catheter 102 to expand, forcing the fluid between the connecting tube 156 and leading end of introducer catheter 102. The fluid will lubricate the connection between the introducer catheter 102 and connecting tube 156 so that the introducer catheter 102 will pull free of the connecting tube 156 thus detaching the inflated balloon assembly from the introducer catheter, which may then be withdrawn.

It will be appreciated that the apparatus and method of the present invention are capable of being incorporated in the form of a variety of embodiments, only a few of which have been illustrated and described above. The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A detachable balloon catheter apparatus comprising:
    an introducer catheter, said introducer catheter having an attachment means at the trailing end thereof for connection to a source of pressurized fluid;
    an inflatable balloon positioned at the leading end of said introducer catheter, said balloon having an opening in fluid communication with the leading end of said catheter; and
    valve means for automatically plugging the opening of said balloon after it is inflated by said pressurized fluid, said valve means comprising an elongated stem that is attached to the interior surface of said balloon.

2. The apparatus of claim 1 wherein a portion of said stem is initially positioned inside the leading end of said introducer catheter and wherein said apparatus further comprises fluid communication means for allowing said pressurized fluid to flow around said stem and into said inflatable balloon.

3. The apparatus of claim 2 wherein said fluid communication means comprise one or more fluid channels formed by ribs on the inside surface of the leading end of said introducer catheter.

4. The apparatus of claim 2 wherein said fluid communication means comprise one or more fluid channels formed by ribs on the outer periphery of said portion of the stem which is initially positioned inside the leading end of said introducer catheter.

5. The apparatus of claim 1 wherein a portion of said stem is initially positioned inside the leading end of said introducer catheter and wherein said portion of the stem has an outside diameter that is sufficiently small in relation to the inside diameter of the leading end of said introducer catheter to permit flow of fluid around said portion of the stem.

6. The apparatus of claim 1 further comprising valve seat means for receiving said valve means in fluid-tight engagement.

7. The apparatus of claim 6 wherein said valve seat means comprise a tubular, elongated leading end that extends into the interior of said balloon and a trailing end that protrudes out of the opening of said balloon and is detachably joined to the leading end of said introducer catheter.

8. The apparatus of claim 7 wherein said stem telescopically extends through the leading end of said valve seat means and is bonded to the interior surface of said balloon, such that said balloon, when inflated, will exert a force on the stem of said valve means that will continuously urge said valve means into fluid-tight engagement with said valve seat means.

9. The apparatus of claim 8 wherein the trailing end of said stem is flared and is joined to an enlarged head portion adapted to engage said valve seat means in a fluid-tight seal.

10. The apparatus of claim 7 further comprising a masking sleeve which fits over the leading end of said valve seat means and which prevents said inflatable balloon from being bonded to said masking sleeve.

11. A detachable balloon catheter apparatus comprising:
a hollow, single lumen introducer catheter having a fitting at the trailing end thereof for connection to a source of pressurized fluid;
an inflatable balloon positioned at the leading end of said introducer catheter, said balloon having an opening that is in fluid communication with the lumen of said introducer catheter; and
valve means for automatically plugging the opening of said balloon after the balloon is inflated to a predetermined amount by said pressurized fluid, said valve means having one end thereof attached to the distal end of said balloon.

12. The apparatus of claim 11 further comprising valve seat means, positioned at the opening of said balloon, for receiving said valve means in fluid-tight engagement.

13. The apparatus of claim 12 wherein said valve seat means comprise a tubular, elongated leading end that extend into the interior of said balloon and a trailing end that protrudes out of the opening of said balloon and is detachably joined to the leading end of said introducer catheter.

14. The apparatus of claim 13 wherein said valve means comprise an elongated stem that telescopically extends through the leading end of said valve seat means and that is bonded to the inside surface of the distal end of said balloon, such that said balloon, when inflated, will exert a force on said stream that will continuously urge said valve means into a closed, fluid-tight position in said valve seat means.

15. The apparatus of claim 14 wherein the trailing end of said stem is flared and is joined to an enlarged head portion which acts to engage said valve seat means in a fluid-tight seal.

16. The apparatus of claim 15 wherein the enlarged head portion of said valve means is initially positioned inside the leading end of said introducer catheter and wherein the leading end of said introducer catheter comprises one or more fluid channels formed by ribs on the inside surface of the leading end of said introducer catheter.

17. The apparatus of claim 15 wherein the enlarged head portion of said valve means is initially positioned inside the leading end of said introducer catheter and wherein ribs are formed on the outer periphery of said enlarged head portion so as to form fluid channels so that said pressurized fluid may flow around said enlarged head portion and into said balloon.

18. The apparatus of claim 15 wherein said enlarged head portion is initially positioned inside the leading end of said introducer catheter and wherein said enlarged head portion is sufficiently small in relation to the inside diameter of the leading end of said introducer catheter to permit flow of fluid around said enlarged head portion.

19. The apparatus of claim 15 further comprising a masking sleeve which fits over the leading end of said valve seat means and which prevents said inflatable balloon from being bonded to said masking sleeve.

20. A detachable balloon catheter apparatus comprising:
a hollow, single lumen introducer catheter having a fitting at the trailing end thereof for connection to a source of pressurized fluid;
an inflatable balloon positioned at the leading end of said introducer catheter, said balloon having an opening that is in fluid communication with the lumen of said introducer catheter;
valve seat means comprising an elongated elastomeric member having a leading end that extends into the interior of said balloon and having a trailing end that protrudes out of the opening to said balloon and is stretched to frictionally fit over the leading end of said introducer catheter;
valve means for automatically engaging said valve seat means in fluid-tight engagement after said balloon is inflated by said pressurized fluid, said valve means comprising an elongated stem that telescopically extends through the leading end of said valve seat means and that is bonded to the distal end of said balloon, said stem having at the trailing end thereof an enlarged head portion adapted to engage said valve seat means in a fluid-tight seal, said enlarged head portion of said stem being initially positioned inside the leading end of said introducer catheter;
fluid communication means for permitting said pressurized fluid to flow around said enlarged head portion of said valve means; and
a collar member which fits over the leading end of said valve seat means and which prevents said inflatable balloon from being bonded to said collar member.

21. In the use of a detachable balloon catheter assembly comprising a single lumen introducer catheter with a fitting at the trailing end thereof for connection to a source of pressurized fluid, an inflatable balloon positioned at the leading end of said introducer catheter, and a valve means positioned at the opening of said balloon, said valve means having one end thereof attached to the interior surface of said balloon, a method of inflating and detaching said balloon from said introducer catheter after it is inflated, the method comprising the steps of:
injecting said pressurized fluid into said balloon so as to inflate the balloon;
automatically plugging the opening to said balloon with said valve means when said balloon is inflated to a predetermined amount; and
thereafter detaching said inflated balloon after it is plugged by said valve means by continued injection of said pressurized fluid.

22. A method as defined in claim 21 further comprising the step of urging said valve means into a closed, fluid-tight position in the opening of said balloon as the balloon is inflated.

* * * * *

UNITED STATES PATENT AND TRADEMARK OFFICE
CERTIFICATE OF CORRECTION

PATENT NO. : 4,311,146
DATED : January 19, 1982
INVENTOR(S) : Wonder

It is certified that error appears in the above-identified patent and that said Letters Patent are hereby corrected as shown below:

On the title page, the name --Gordon S. Reynolds-- should be included as one of the inventors.

Column 1, line 60, "to data" should be --to date--

Column 2, line 2, "7Surgical" should be --7 Surgical--

Column 2, line 3, "The technique" should be --This technique--

Column 5, line 8, "The valve mechanism 103" should be --The valve mechanism 104--

Column 5, line 62, "Could be performed" should be --could be preformed--

Column 7, line 22, "104 wll be withdrawn" should be --104 will be withdrawn--

Column 7, line 34, "102 will force th collar" should be --102 will force the collar--

Signed and Sealed this

Ninth Day of August 1983

[SEAL]

Attest:

GERALD J. MOSSINGHOFF

*Attesting Officer*     *Commissioner of Patents and Trademarks*